United States Patent [19] [11] 4,449,973
Luther [45] May 22, 1984

[54] SMALL GAUGE, PRE-SPLIT CANNULA AND PROCESS FOR MANUFACTURE

[75] Inventor: Ronald B. Luther, Newport Beach, Calif.

[73] Assignee: Luther Medical Products, Inc., Costa Mesa, Calif.

[21] Appl. No.: 397,059

[22] Filed: Jun. 26, 1982

[51] Int. Cl.³ ............................................. A61M 5/32
[52] U.S. Cl. ................................... 604/161; 604/272
[58] Field of Search .............................. 604/158–170, 604/280, 272

[56] References Cited

U.S. PATENT DOCUMENTS

| | | | |
|---|---|---|---|
| 3,359,978 | 12/1967 | Smith | 604/161 |
| 3,382,872 | 5/1968 | Rubin | 604/161 |
| 3,766,915 | 10/1973 | Rychlik | 604/161 |
| 4,147,165 | 4/1979 | Tauschinski | 604/161 |
| 4,306,562 | 12/1981 | Osborne | 604/280 |
| 4,377,165 | 3/1983 | Luther et al. | 604/160 |
| 4,411,654 | 10/1983 | Boarini et al. | 604/165 |

FOREIGN PATENT DOCUMENTS 528271 11/1972 Switzerland .

Primary Examiner—Dalton L. Truluck
Attorney, Agent, or Firm—Willie Krawitz

[57] ABSTRACT

A small size cannula having internal grooves is produced by pre-splitting the proximal end of the cannula along the grooves, and mounting the split ends into plastic, breakaway wings. By means of the split ends, mounting of the cannula into the wings is greatly facilitated. The process also permits the grooves to be formed along the barrel of the cannula in a random fashion, which entails less manufacturing expense.

Following insertion of the cannula into a patient, the catheter is fed through the cannula into the patient, and the cannula is withdrawn. The pre-split cannula is then broken or split away from the catheter using the wings. Since less force is required to initiate splitting of the cannula, shallower grooves can be used, and this results in a greater structural integrity for cannula of smaller sizes.

11 Claims, 6 Drawing Figures

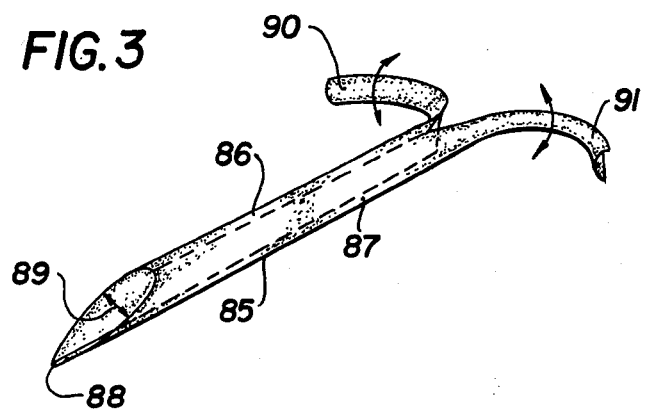
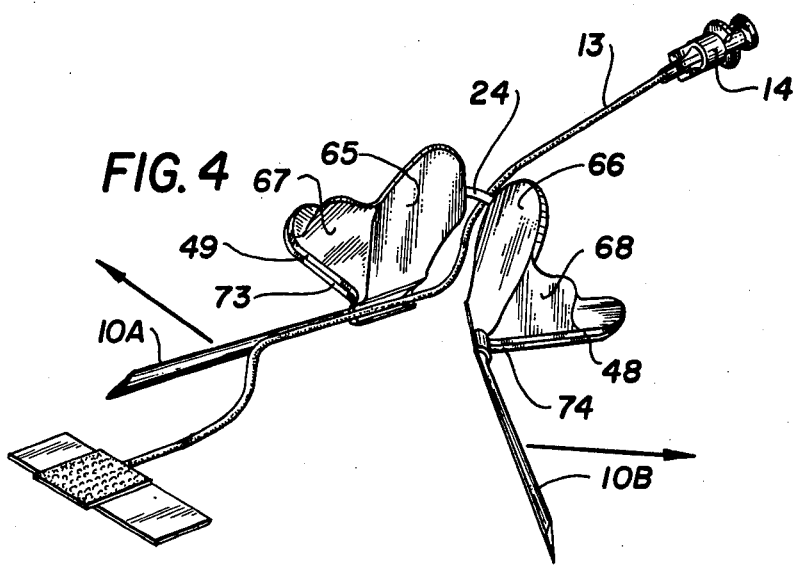
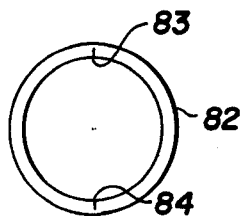
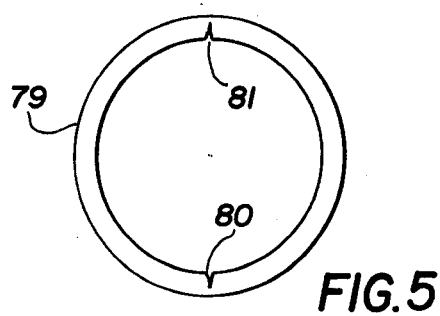

SMALL GAUGE, PRE-SPLIT CANNULA AND PROCESS FOR MANUFACTURE

BACKGROUND OF THE INVENTION

This invention relates to a new and improved small size, breakaway cannula and the process for its manufacture. More specifically this invention provides a breakaway cannula of improved structure for its size that can be mounted inexpensively in low cost, breakaway wings.

Typical publications disclosing breakaway cannula and their manufacture are found in U.S. Pat. No. 3,359,976 to Raymond M. Smith; Swiss Pat. No. 528,271 to Heinz Fuchs and Arthur Eschbach (Nov. 15, 1972); and, U.S. Pat. No. 4,100,393 to Ronald B. Luther.

In the Smith patent, a stamping operation is used to provide the cannula and wing pattern followed by rolling the pattern to the desired cannula shape with integral wings. In the Swiss patent, plastic wings are attached to the proximal end of the cannula by means of an injection molding machine to reduce operating costs and to facilitate splitting the cannula from the proximal end when in use. The Luther patent describes a laser welding operation to attach metal wings to the cannula.

The above types of manufacturing processes for attaching gripping wings to breakaway cannula are suitable if the cannula size is larger than 14 gauge, i.e. larger than about 0.09 inches. However, when manufacturing cannula shown in the Swiss Patent in small sizes of, say, 14–35 gauge diameter, it becomes more difficult to join the wings to the proximal end of the cannula using injection molding techniques. Similarly, both laser welding and pattern stamping techniques become considerably more difficult and time consuming when working with such small cannula.

Another problem associated with a breakaway cannula needle is that it becomes structurally weaker with decreasing size. This situation is aggravated when weakening breakaway grooves are machined or rolled along the cannula itself or on the pre-cannula flatstock. If the weakening grooves could be made smaller, or if the cannula needle wall thickness could be increased, or both, the cannula would of course be stronger.

Still another problem associated with producing grooved cannula is that the cannula must be oriented relative to their grooves prior to sharpening the needle end. This is because the grooves are designed to coincide with the forward and trailing points of the needle. It would be preferred to form and sharpen the needle portion of the cannula without regard to the specific location of the grooves.

Many physicians desire to aspirate blood through the cannula and into the catheter, but this of course, is not possible if a slit cannula is used. If a continuous cannula (i.e. one having no slit) is used instead, it becomes difficult to split away from the catheter. It would be preferred to employ a cannula that can be easily split open, but has a continuous surface with no slit.

THE INVENTION

According to the invention, there is provided a new and improved pre-split cannula having a diameter of smaller size than 14 gauge. During manufacture, the proximal end of the cannula is pre-split and the free ends are mounted in plastic wings; when the wings are folded together, a rigidifying barrel-like enclosure is formed around the proximal end of the cannula. Hence, when the needle is withdrawn from the patient and the wings are opened, the attached cannula is split in half. Because the proximal end is pre-split by machine, the inertia required to continue the splitting process by hand, when in use, is greatly reduced.

The cannula is provided with one or more, say two or three, weakening grooves along the barrel interior, the grooves being formed on flatstock prior to rolling. The groove angle may be calculated so that upon rolling into the cannula barrel, an open groove form is still retained; alternatively, the grooves may be formed as a partial slit. A subsequent hardening by cold drawing of the cannula barrel into a smaller diameter will then cause this slit to partially close, thereby improving the cannula strength, without unduly impairing its splitting capability.

Because of its small gauge, the free proximal ends of the cannula can be readily manipulated, such as by twisting. Hence, the cannula can be oriented randomly for needle grinding with respect to the grooves, and the free proximal ends can be twisted from any orientation and mounted into the wing holders. The central portion of the needle can thereby be aligned centrally of the wing holders, and this simplifies production.

BRIEF DESCRIPTION OF THE DRAWINGS

FIG. 3 is an upper perspective view of another embodiment of the cannula;

FIG. 4 is an upper perspective view of the cannula and gripping wing device after breaking away from a catheter; and, FIGS. 5 and 6 show cross sectional views of the cannula, taken perpendicular to the longitudinal axis of the cannula, and illustrate different types of weakening groove configurations;

DESCRIPTION OF THE PREFERRED EMBODIMENTS

Figure 1:
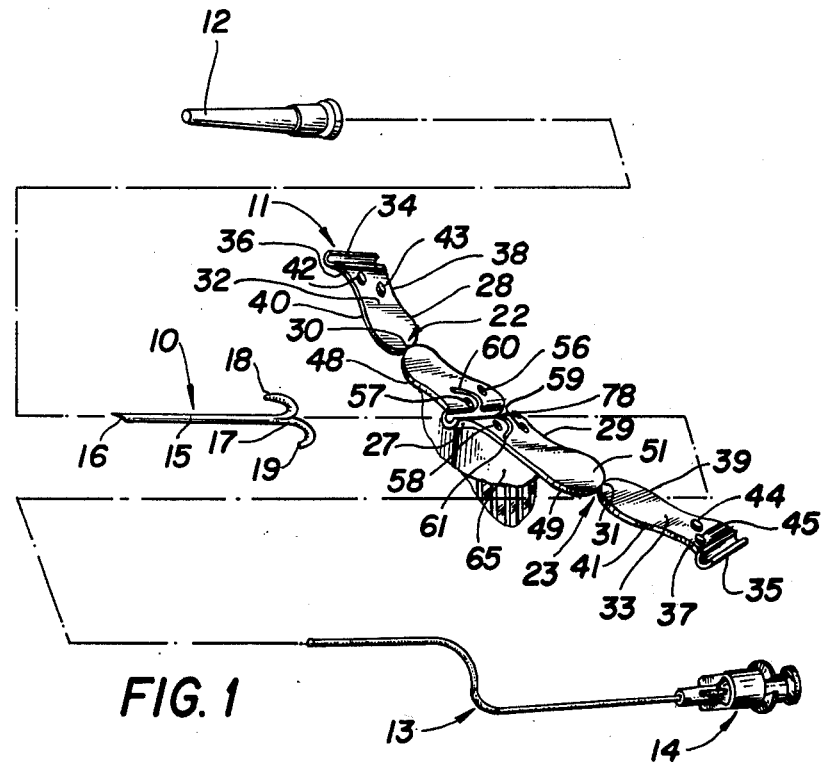
FIG. 1 is an upper perspective, exploded view of the disassembled cannula and gripping wing device of this invention.

The cannula 10 and gripping wings 11 of this invention, including a cannula cover 12, catheter 13 and attached hub 14 are shown disassembled in FIG. 1.

The cannula 10 includes a barrel portion 15, needle or distal end 16, and a proximal end 17, that is pre-split into hook or curved elements 18, 19. The cannula defined internal grooves 20, 21 along its longitudinal axis which are formed by means of a roller or diamond scribe, etc., that is moved along metal flatstock under constant pressure to produce a uniform groove depth. The metal flatstock is then rolled into the round cannula configuration and laser welded to form its final continuous shape. As shown in FIGS. 5 and 6, the grooves are parallel to each other, and about 180° radially separated therefrom.

The plastic gripping wings 11 to which the cannula is mounted, are shown in the unfolded state in FIG. 1. These wings are injection molded using a plastic such as polypropylene, nylon, polyester, or any other suitable sterilizable material. The gripping wings 11 comprise twin elements 22, 23 that may be joined by a thin, breakable strip of material 24. When the wings are open, and the cannula is mounted therein, a half barrel element 27 is formed around the proximal end 17 of the cannula.

Each twin element 22, 23 includes outer hinge elements 28, 29 that fold about hinges 30, 31. The outer hinge elements comprise a flat base 32, 33 having a peripheral groove portion 34, 35, inclined edges 36, 37 and upper and lower curved edges 38, 39 and 40, 41. Mounting pins 42, 43 and 44, 45 extend outwardly from the hinge elements, and are integrally formed therewith.

The bases 48, 49 of the gripping wing elements 22, 23 have flat areas 50, 51. The bases are contoured along their flat areas and edges to register with the corresponding outer hinge elements 28, 29 when the outer hinge elements are folded over about their respective hinges 30, 31. The bases provide bores 56, 57 and 58, 59 to engage the pins 42, 43 and 44, 45 respectively and secure the hinge elements 28, 29 in place when these hinge elements are folded over. Grooves 60, 61 are inscribed along the surfaces 50, 51 and are shaped to engage the curved or hook shaped elements 18, 19 of the cannula 10.

Figure 2:
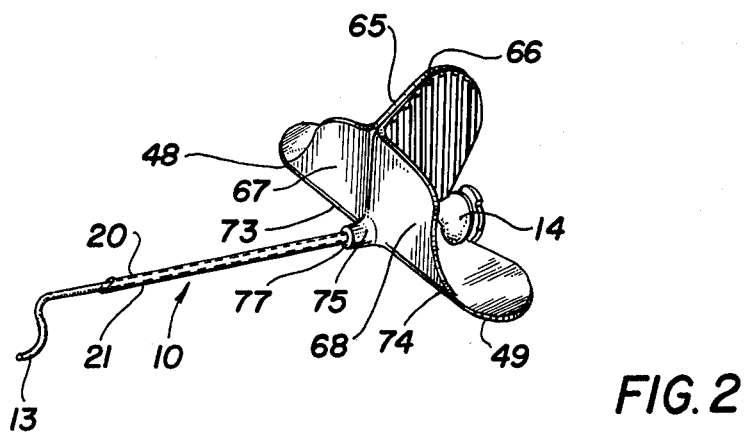
FIG. 2 is an upper perspective view showing the cannula assembled with the gripping wing device.

As shown in FIGS. 2 and 4, gripping wings 65, 66 are integrally formed with each base 48, 49 and are attached to one end of each base by reinforcing elements 67, 68. Also, each gripping wing is secured by the reinforcing elements to the leading edge 73, 74 of each base.

Installation of a cannula into a gripping wing 11 is preferably made at the factory and involves insertion of the cannula hook elements 18, 19 into the grooves 60, 61 of the bases 48, 49. The outer hinge elements 28, 29 are folded along hinges 30, 31 and the mounting pins are pressured and locked into their respective bores. It will be appreciated that the pin and bore lock may be replaced by sonic welding, adhesives, by heating and embedding the heated elements into the plastic material of the wings, etc. The flat bases 32, 33 of the hinge elements 28, 29 will then register with the respective flat areas 50, 51 of the bases 48, 49 and secure the hook shaped elements 18, 19 of the cannula in place. To further improve cannula rigidity within the gripping wings, the peripheral grooves 34, 35 mate with the half barrel element 27 to form a split ring barrel enclosure 75 around the proximal end of the cannula. The barrel enclosure projects a short distance along the proximal end 17 of the barrel to form a fitting element 77 that encases the cannula cover 12.

When the cannula and gripping wings are finally assembled, a circularily tapered cut-out section 78 is formed rearwardly of the barrel enclosure 75 and typically is about ⅜" long. When the catheter 13 is inserted into the cannula, the attached hub 14 will fit securely into the cut-out section 78 and will prevent loss of the catheter into the patient and the problem of catheter embolism.

As shown in FIG. 4, when the cannula 10 is withdrawn from the patient, it is split in half by separating the gripping wings 65, 66 in the direction shown by the arrows. This enables the cannula halves 10A, 10B to be separated from the catheter 13.

Excellent stiffness, splitting and rolling properties are obtained with a flatstock thickness of about 2-8 mils, a cannula length of about ¾"-6", about a 14-36 gauge barrel diameter, and a uniform groove depth of about 30%-60% of the flatstock thickness using a 304-316 stainless steel or equivalent.

The flatstock may be in a flat form such as in sections, say, ½-10 feet long, but is usually loaded on a roll. The open needle portion constitutes only up to about 15% of the total cannula length. Thus, the cannula of this invention can employ a relatively deeper groove and still maintain structural integrity during use.

FIGS. 5 and 6 illustrate two types of grooves that may be employed with the cannula of this invention. In FIG. 5, the cannula 79 is provided with two internally disposed, open grooves 80, 81 that may have, say, a V, U-shaped or rectangular shape. In FIG. 6, the cannula 82 has two internal grooves 83, 84 that have the appearance of closed slits after the cannula has been reduced in diameter by cold drawing.

FIG. 3 illustrates a cannula 85 produced by the process of this invention, in which the internal grooves 86, 87 are oriented randomly and misaligned with respect to the needle 88 and open end 89. The free ends 90, 91 of the cannula are subsequently twisted in the direction shown by the arrows so that the needle 88 and open end 89 will be centrally aligned with the gripping wings when mounted therein. The production technique of random groove orientation with respect to the needle simplifies the manufacturing process, and hence, reduces production costs. Also, the manufacturing process that produces the free cannula ends and secures them in the wing mounting is related to the subsequent use of the cannula, in that the splitting process is continued by means of separating the free ends.

The cannula of this invention has the unique features of being internally grooved and closed, and can be easily split without requiring a slit. The nature of the cannula and the use of plastic wings dispenses with the need for a wing welding operation and related equipment. Also, the need to align the barrel and grooves when sharpening the needle is eliminated.

I claim:

1. A cannula needle for insertion of a catheter therethrough, comprising:
    A. A cannula including: a barrel portion having a longitudinal axis, distal and proximal ends, and internal and external walls;
        i. one or more weakening grooves formed along the internal wall and parallel to the longitudinal axis;
        ii. the barrel portion being produced by the sequential steps of grooving flatstock having parallel edges, and a thickness of about 2-8 mils, rolling the flatstock to form the barrel, and reducing the barrel in diameter to form a 14-36 gauge barrel diameter of continuous shape, closed, registered edges, and closed grooves in the internal wall, a cannula length of about ¾"-6", and a uniform groove depth of about 30%-60% of the flatstock thickness using a 304-316 stainless steel, the barrel being work hardened, and the grooves and enclosed edges being embrittled by rolling and cold drawing;
        iii. pre-split proximal ends and a needle portion being formed on the barrel; and,
    B. separable wing holders, including a reinforcing barrel surrounding the proximal end of the cannula, a pre-split end being mounted within a separate wing; whereby,
        i. during use, the cannula is adapted for minimal leakage of blood through the closed edges and grooves and for aspiration of blood through the cannula; and, ii. following use, the cannula is adapted to be split open, commencing from the proximal ends and continuing along the grooves, thereby enabling the cannula to be separated from the catheter, the wing holders being adapted to secure each pre-split end of the cannula when being split open.

2. The cannula of claim 1, in which the grooves are separated by about 180°.

3. The cannula of claim 1, in which the grooves are oriented randomly with respect to the needle and proximal ends of the cannula.

4. The cannula of claim 1, in which the catheter includes an attached hub that fits into the reinforcing barrel.

5. The cannula of claim 1, in which the wings are plastic.

6. The cannula of claim 1, in which the barrel diameter is greater than 36 gauge.

7. The cannula of claim 1, in which the flatstock is rolled into the cannula shape, welded, and then cold drawn.

8. The cannula of claim 1, in which the separable mounting means comprise an injection molded plastic, including:
  i. matched support members, each of said members providing a flat surface, a groove for seating a pre-split engaging end, a barrel segment adjacent the groove, and closure means;
  ii. matched closure members, each of said members providing a flat surface, a barrel segment, and means for effecting closure with the support member;
  iii. gripping means downwardly dependant from each support member, and being attached thereto adjacent the groove and barrel segment;
and,
  iv. reinforcing means integrally formed with the gripping means and inner support members;
whereby, when the pre-split ends are seated in the grooves, and the closure members and support members are then closed together, the flat surfaces of corresponding support and closure members will register and secure the pre-split ends within the grooves, and the proximal end of the cannula is secured within the barrel segments of the support and closure members.

9. The cannula of claim 1, in which The grooves in the cannula are slit shaped.

10. The cannula of claim 1, in which the grooves in the cannula are open shaped.

11. The cannula of claim 1, in which the cannula defines an open needle portion up to about 15% of the total cannula length.

* * * * *